United States Patent

Tenerz et al.

[11] Patent Number: 6,106,486
[45] Date of Patent: Aug. 22, 2000

[54] GUIDE WIRE

[75] Inventors: Lars Tenerz; Per Egneloev, both of Uppsala, Sweden

[73] Assignee: Radi Medical Systems AB, Uppsala, Sweden

[21] Appl. No.: 08/996,038

[22] Filed: Dec. 22, 1997

[51] Int. Cl.[7] .................................................. A61B 5/00
[52] U.S. Cl. ........................... 600/585; 604/96; 604/280
[58] Field of Search .................................. 600/585, 561, 600/407, 443

[56] References Cited

U.S. PATENT DOCUMENTS

| | | | |
|---|---|---|---|
| 4,023,562 | 5/1977 | Hynecek et al. | 128/2.05 E |
| 4,274,423 | 6/1981 | Mizuno et al. | 128/675 |
| 4,850,358 | 7/1989 | Millar | 128/637 |
| 5,226,423 | 7/1993 | Tenerz et al. | 128/673 |
| 5,309,910 | 5/1994 | Edwards et al. | 128/642 |
| 5,404,753 | 4/1995 | Hecht et al. | 73/204.22 |
| 5,445,155 | 8/1995 | Sieben | 600/443 |
| 5,447,073 | 9/1995 | Kalinoski | 73/861.24 |
| 5,715,817 | 2/1998 | Stevens-Wright et al. | 600/585 |

FOREIGN PATENT DOCUMENTS

| | | |
|---|---|---|
| 9603217 2 | 8/1997 | Sweden . |
| WO 97/27802 | 8/1997 | WIPO . |

*Primary Examiner*—Cary O'Connor
*Assistant Examiner*—Pamela L. Wingood
*Attorney, Agent, or Firm*—Foley & Lardner

[57] ABSTRACT

A guide wire for intravascular investigations includes an elongated element, and electrical conductors extending along a length of the guide wire. A portion of one of the electrical conductors is provided as a layer of electrically conductive material, extending concentrically over the circumference of, and along the elongated element forming a part of the guide wire.

A method of manufacturing a conductor element for a guide wire with conductors in the form of a layer of a conductive material extending along the length of the conductor element is provided. A core element is provided. Overlapping layers of alternating insulating and conductive materials are applied concentrically around the circumference of the core element along a portion of its length, until a desired number of conductive layers have been applied.

15 Claims, 8 Drawing Sheets

GUIDE WIRE

BACKGROUND OF THE INVENTION

The present invention relates to a guide wire for intravascular investigations, provided with electrical conductors along its length.

In a further aspect the invention relates to a proximal male connector for a guide wire. The invention also relates to a method of manufacturing a guide wire.

A male connector and a guide wire of the type identified in the preamble are disclosed in U.S. patent application Ser. No. 08/9028,677, Akerfeldt et al., entitled "Male connector with a continuous surface for a guide wire and method therefor" ("Akerfeldt") (assigned to the same assignee as the present application) (expressly incorporated herein).

One problem with guide wires of the type disclosed in said application is the extremely difficult manual assembling procedure required to make these devices. The extremely small components must be assembled under microscope, which is very tedious and labor intensive.

Another problem with guide wires of this type is to make them rotationally symmetric to the greatest extent possible. This is desirable in order that the manipulation of the guide wire in the blood vessels be independent of the direction of movement of the wire during insertion. This is a difficult task if separate wires are provided in the guide wire along its length, which is the commonly adopted technique today.

The guide wire disclosed in Akerfeldt is made by imbedding discrete electrical leads in a plastic sleeve, which provides insulation between the leads and a core wire around which the sleeve is provided, and a smooth surface.

There are several advantages with this design over the designs previously known, such as, for example there is a reduced risk of electrical short-circuiting and also it is easy to clean the surface from blood by virtue of it being smooth.

Although the connector and guide wire disclosed in Akerfeldt represents improvements in connector and guide wire design, there is still the disadvantage of the devices having to be assembled manually to a very great extent, and not being fully rotationally symmetric.

SUMMARY OF THE INVENTION

For the purpose of this application the term "distal portion" will have the meaning of that part of a guide wire extending from the distal tip, where the illustrated core wire has a reduced diameter, and along the entire portion of the guide wire where the diameter is reduced.

Correspondingly the term "proximal portion" will have the meaning of that part of a guide wire extending from the proximal end and towards the distal end where the core wire has a nominal diameter larger than the diameter of the distal portion.

Furthermore, for the purposes of this application, the term "circumferential" or "extending circumferentially" shall mean that a layer extends at least over a major part of the circumference of an element forming a part of a guide wire.

The present invention seeks to provide an improved guide wire and connector wherein the disadvantages of prior art devices are overcome.

Thus, an object of the present invention is to provide a guide wire with electrical conductors, which is suitable for batch manufacture.

Another object of the invention is to provide a guide wire having a bending moment that is equal in all directions.

This is achieved by providing a guide wire according to claim 1, by arranging one or more electrical leads as concentric layers of conductive material around a core wire, with insulating layers between said conductive layers.

An important advantage with this design is that it will be very much easier to manufacture a guide wire according to the invention; especially it will become possible to make guide wires in batches.

Another advantage is that the guide wire becomes fully rotationally symmetric, rendering the bending moment of the guide wire equal in all directions. This will in particular eliminate the tendency to "flip" when the wire is rotated inside the vessel. "Flipping" is an effect caused by the bending moment being higher along a lead that is drawn parallel to the core wire. Namely, the wire bends easier in a direction where no electrical lead is present than where there is one.

In a preferred embodiment wherein the guide wire is made without a protective proximal tube, also the tendency with prior art guide wires to break in the proximal region, i.e., the tendency of the proximal protective tube to break, is reduced or even eliminated. This is because the torsional or twisting moment is greater.

In one embodiment also the core wire is used as an electrical lead, which makes it possible to further reduce the external diameter of the entire guide wire assembly.

Also in accordance with the invention, a proximal contact is very easily provided on the guide wire. It is especially advantageous from a production cost viewpoint, that many of the very tedious and elaborate assembling procedures necessary for making proximal contacts for the prior art devices are eliminated.

In a further embodiment the guide wire is provided with an electrical sensor at its distal end, connection between said sensor and said electrical leads being made by bonding electrical wires to exposed portions of said concentric layers, thus forming contact pads.

An alternative way of bonding is by providing the required number of contact surfaces on a sensor chip and making direct contact by bonding to said exposed portions of said concentric layers. Thereby it is possible to eliminate the separate electrical wires, which are difficult to mount by virtue of the extremely small dimensions involved.

Instead of wires a small flexible circuit board may be provided as a bridge between the sensor and the contact members on the exposed layer portions.

The guide wire is manufactured by providing a core wire, that may or may not be electrically conductive, with alternating layers of insulating and conductive materials, until the desired number of conductors has been obtained. The conductive layers may be applied by various thin film techniques, such as CVD, PVD, sputtering, evaporation electrical plating, chemical (electroless) plating. The insulating layers may be applied by evaporation, CVD, dipping, spray or combinations of these.

The proximal contact is easily made according to the invention by either of two methods, namely by masking selected portions during coating of the respective concentric layers, or by removing the selected portions of said layers by etching and dissolving away, respectively.

The guide wire according to the invention having conductors extending along its length, will in fact be as simple to manufacture as a conventional guide wire with no electrical function at all.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus not limitative of the present invention, and wherein.

DETAILED DESCRIPTION OF THE PREFERRED EMBODIMENTS

Figure 1:
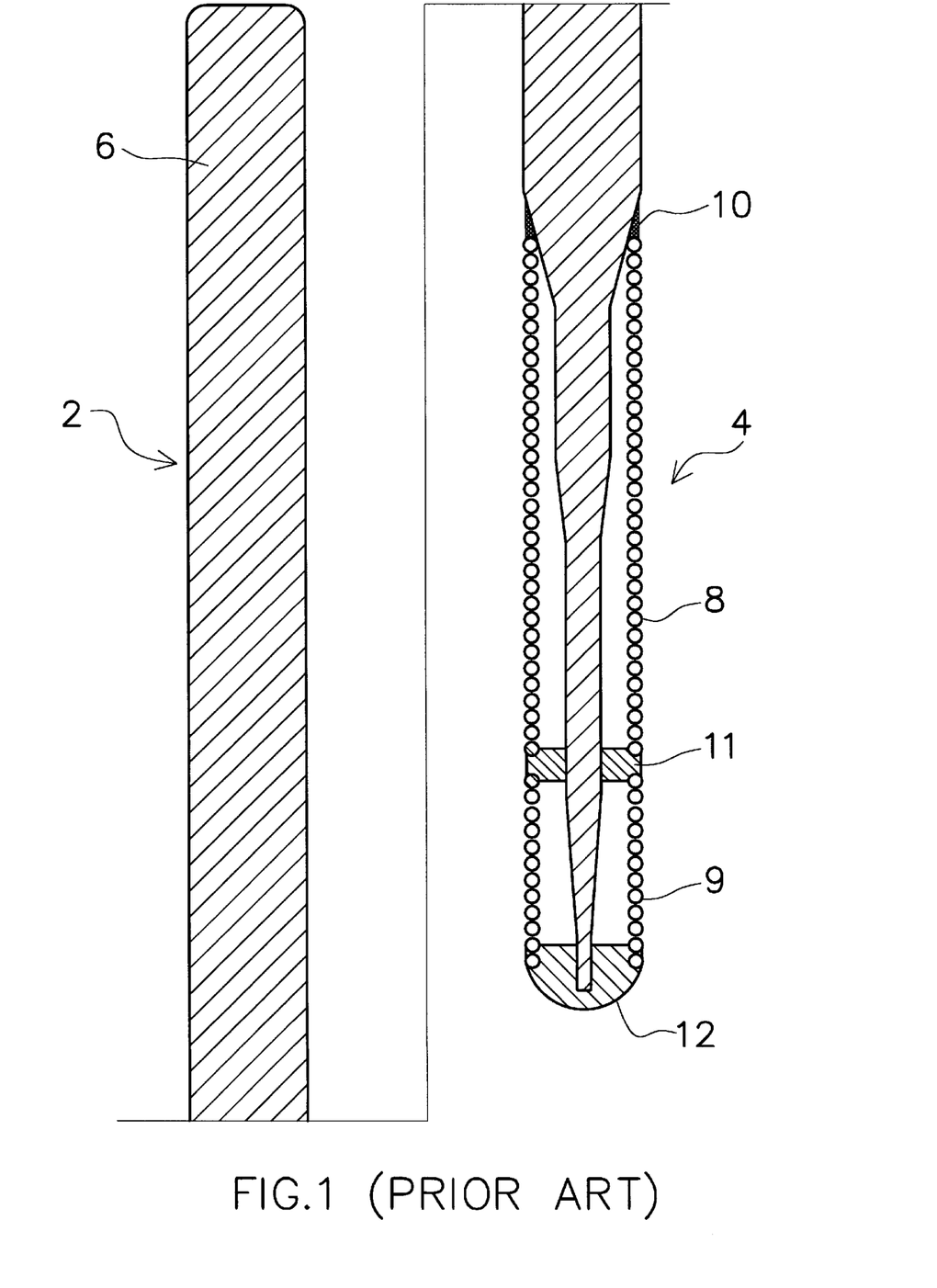
FIG. 1 illustrates in cross section a prior art guide wire having no electrical functionality.

In FIG. 1 the proximal 2 and distal 4 ends of a conventional guide wire having no electrical functionality are shown. Such a guide wire is used for guiding catheters to a desired spot in a body vessel for various purposes. It comprises a core wire 6 which has a uniform diameter along the main part of its length (about 1400 mm), and at the distal end 4 the core wire has a reduced diameter. A coil 8 made of stainless steel is positioned over the narrow distal part of the core wire 6, except for the very tip portion, which is covered by a further coil 9 made of Pt. The coils 8 and 9 are joined by solder 11. The coil is secured to the core wire by soldering 10, and the tip of the core wire is secured in an end stopper 12, e.g. make of solder.

Figure 2:
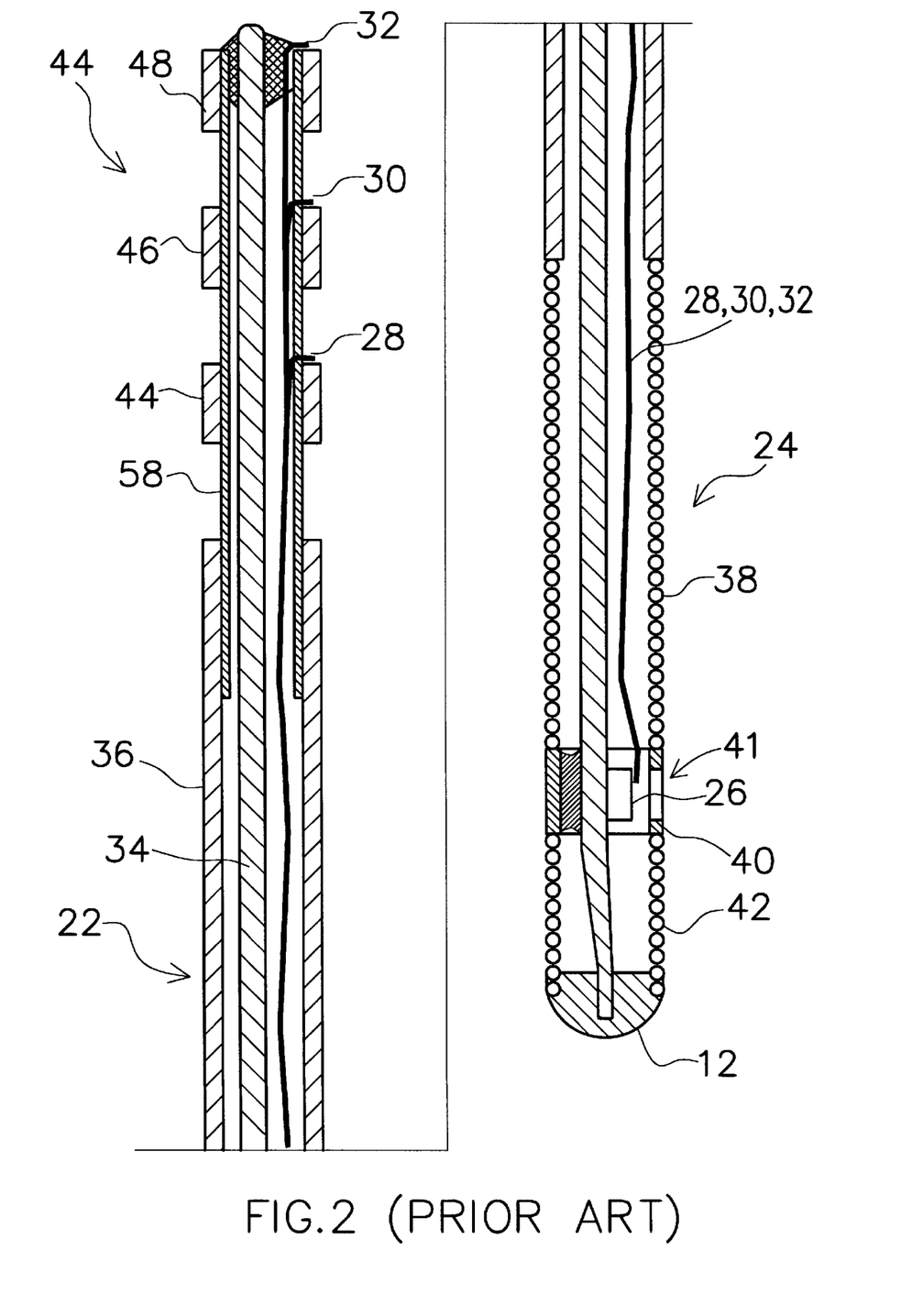
FIG. 2 illustrates in cross section a prior art guide wire having an electrical sensor mounted in the distal end.

In FIG. 2 there are shown the proximal 22 and distal 24 ends of a prior art guide wire having electrical functionality in the form of a pressure sensor 26 mounted in the distal tip of the guide wire. The guide wire comprises a core wire 34 surrounded by a tube 36. The electrical signals from the sensor are transmitted via electrical leads 28, 30, 32 (only one of which is seen in the figure) provided in the space between the core wire 34 and the tube 36. In the distal portion a coil 38 is provided as an extension of the tube 36. In the region of the sensor 38 there is provided a piece of protective tube 40 with an aperture 41 for exposing the sensor 26 to the environment. On the distal side of said protective tube 40 there is provided a further piece of coil 42. The very tip is terminated in the same way as the conventional guide wire of FIG. 1, e.g. with a small spot of solder 12.

At the proximal end 22 the guide wire is provided with a male connector 44. That is, the wires 28, 30, 32 each terminate in a ring shaped contact element 44, 46, 48, respectively. The ring shaped contacts are mounted on an insulating tube 58. The contacts are arranged in a spaced apart relationship, such that corresponding mating contact elements of a female connector can engage and provide electrical contact.

Figure 3:
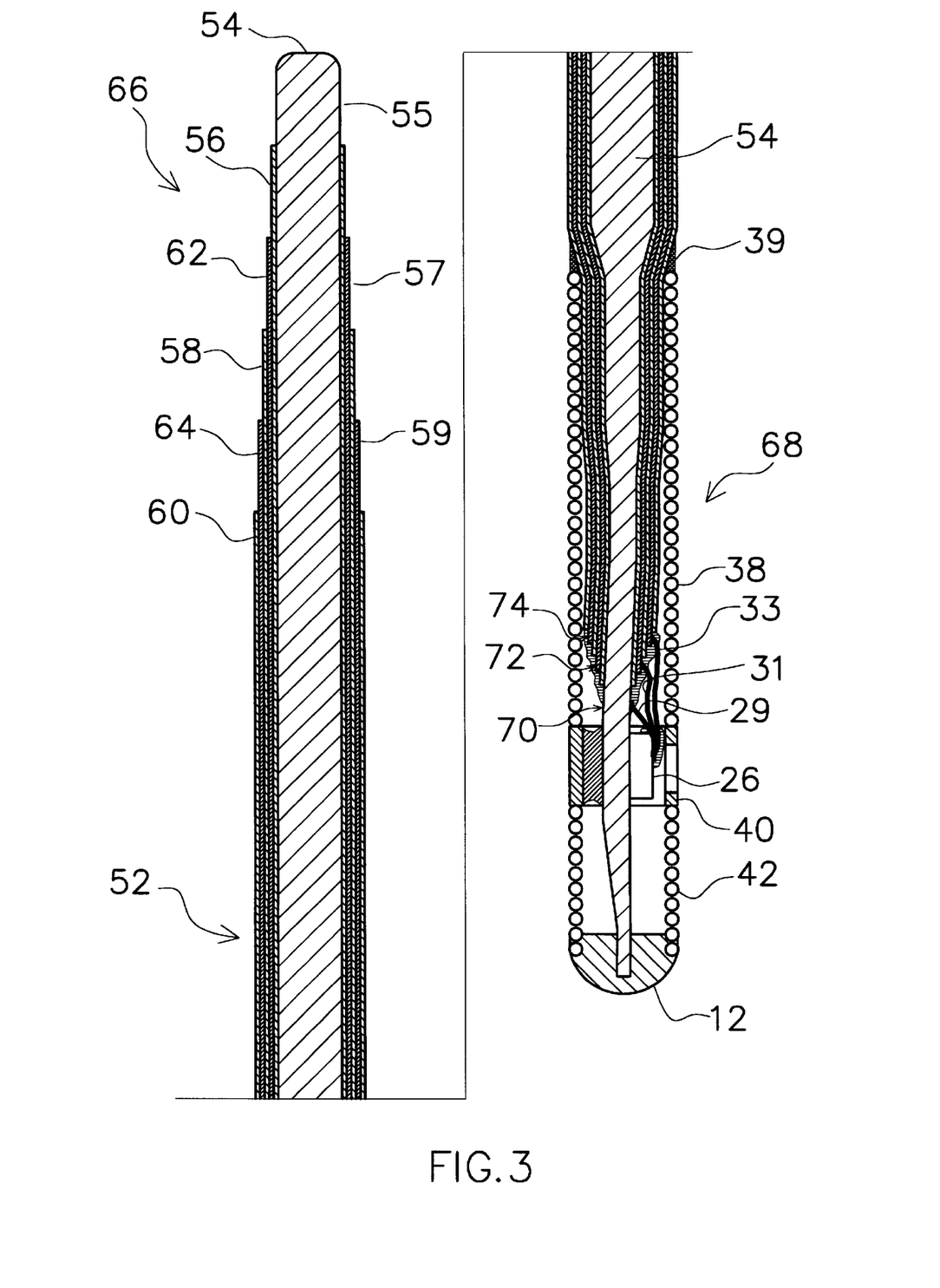
FIG. 3 is a view in cross section of a guide wire according to the present invention, where only the proximal and distal ends are shown.

With reference now to FIG. 3, a preferred embodiment of a guide wire according to the present invention, generally identified with reference numeral 52, and featuring the novel structure of electrical conductors, is shown.

The guide wire comprises a core wire 54 made of a conductive material, e.g. steel. The core wire is covered by concentric layers of alternatingly insulated material 56, 58, 60 and conductive material 62, 64.

The proximal end portion 66 is designed such as to form a male contact member, which will be described in further detail below.

The distal end 68 has similarly been formed to comprise contact elements 70, 72, 74 for the connection of an electrical sensor element 26, similar to the one disclosed in FIG. 2. The sensor element 26 is connected to the contact members 70, 72, 74 via electrical wires 29, 31, 33 for example by bonding or soldering or other suitable means.

It should be noted that in this embodiment the core wire 54 is used as one conductor, hence contact element 70 is simply an exposed portion of said core wire 54.

In the embodiment of FIG. 3, the distal end portion 68 of the core wire 54 preferably has a reduced diameter. The reduced diameter is advantageously achieved by grinding. This smaller diameter portion has a length of about 300 mm. A coil 38, similar to that shown in FIG. 2, has been provided over this portion in order to give the desired flexibility and torsional strength. The coil 38 is attached to the core wire in the region where the diameter is reduced by gluing 39 or other suitable attachment means.

The portion having the larger diameter is preferably a conventional length, i.e., about 1400 mm long. The outer insulating layer 60 forms the contact surface towards the exterior environment, i.e. blood inside the vessel in which the guide wire is inserted. In the figure this layer 60 is shown to have the same thickness as the other layers 56, 58, but may be made thicker or thinner if the material properties should so require in order to give the guide wire the required extent of protection against the influence of the environment. The outer layer 60 could also be formed by providing a shrink-tube over the guide wire.

The core wire 54 advantageously may be manufactured from stainless steel (309 V grade) or "surgical grade" stainless steel, if it is to be used as a conductor, as in the shown embodiment. Other conductive materials are conceivable, provided that the required compromise between stiffness and flexibility is obtained. The guide wire as a whole must be stiff enough to be easily inserted into the vessel, and flexible enough that it adapts smoothly to the bends inside the vessels without causing damage.

At the proximal end 66 of the guide wire 52, the conductive layers have been exposed in a consecutive manner, thereby forming contact surfaces 55, 57, 59 extending circumferentially around the core wire 54. These circular contact surfaces, forming contact members, are suitable for engagement with a female connector, such as the one disclosed in Swedish patent application 9701108-4 (corresponding to U.S. provisional application Ser. No. 60/042,394). In the figure the step configuration of the contact members is exaggerated. In reality the entire contact region, including contact members 55, 57, 59 to be engaged by a female connector may be regarded as a flat surface, and will be experienced as such by the female connector.

Figure 4:
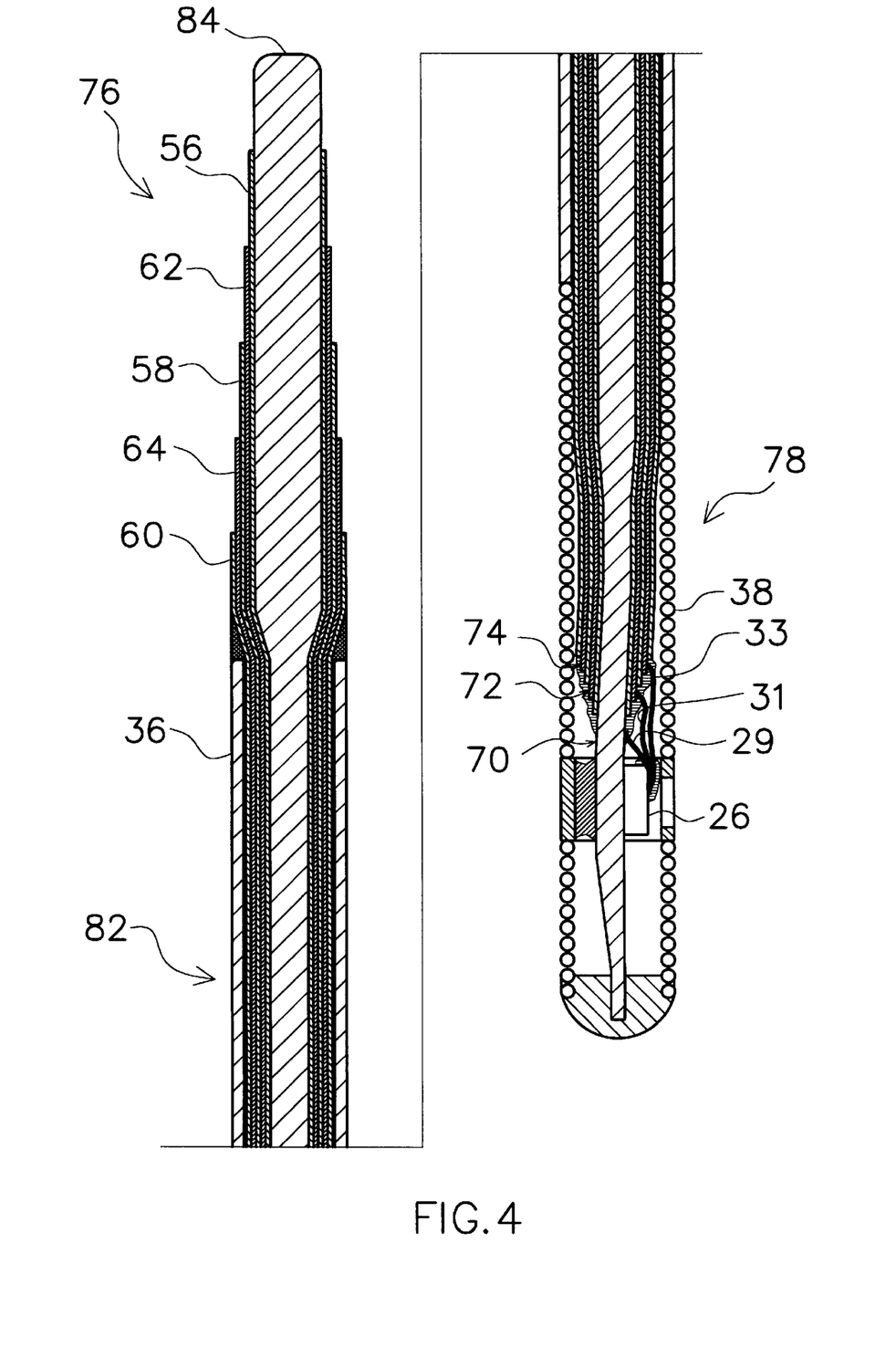
FIG. 4 is a view in cross section of another embodiment of a guide wire according to the present invention, where only the proximal and distal ends are shown.

In an alternative embodiment of the guide wire 82, shown in FIG. 4 (like elements have been given the same reference numerals), the proximal part 76 of the core wire 84 having the larger diameter is only a few centimeters long, and the major part (constituting the distal portion as defined above) of the core wire 84 has a smaller diameter and extends over a length of about 1400 mm. In this embodiment there is provided an outer protective tube 36, like in the prior art device of FIG. 2, which extends over essentially the entire length, apart form the distal end 78 which is covered by a coil 38, like in the embodiment of FIG. 3.

As can be seen in both FIG. 3 and FIG. 4, the distal end 68, 78 of the core wire 54, 84 has a portion in the tip region with reduced diameter where the previously mentioned contact members 70, 72, 74 are provided. In the embodiments shown the sensor chip 26 is mounted on the core wire 54, 84, for example by gluing, and electrical leads 29, 31, 33 are used to make contact with the conductors 62, 64 provided on the core wire 54, 84.

Figure 5:
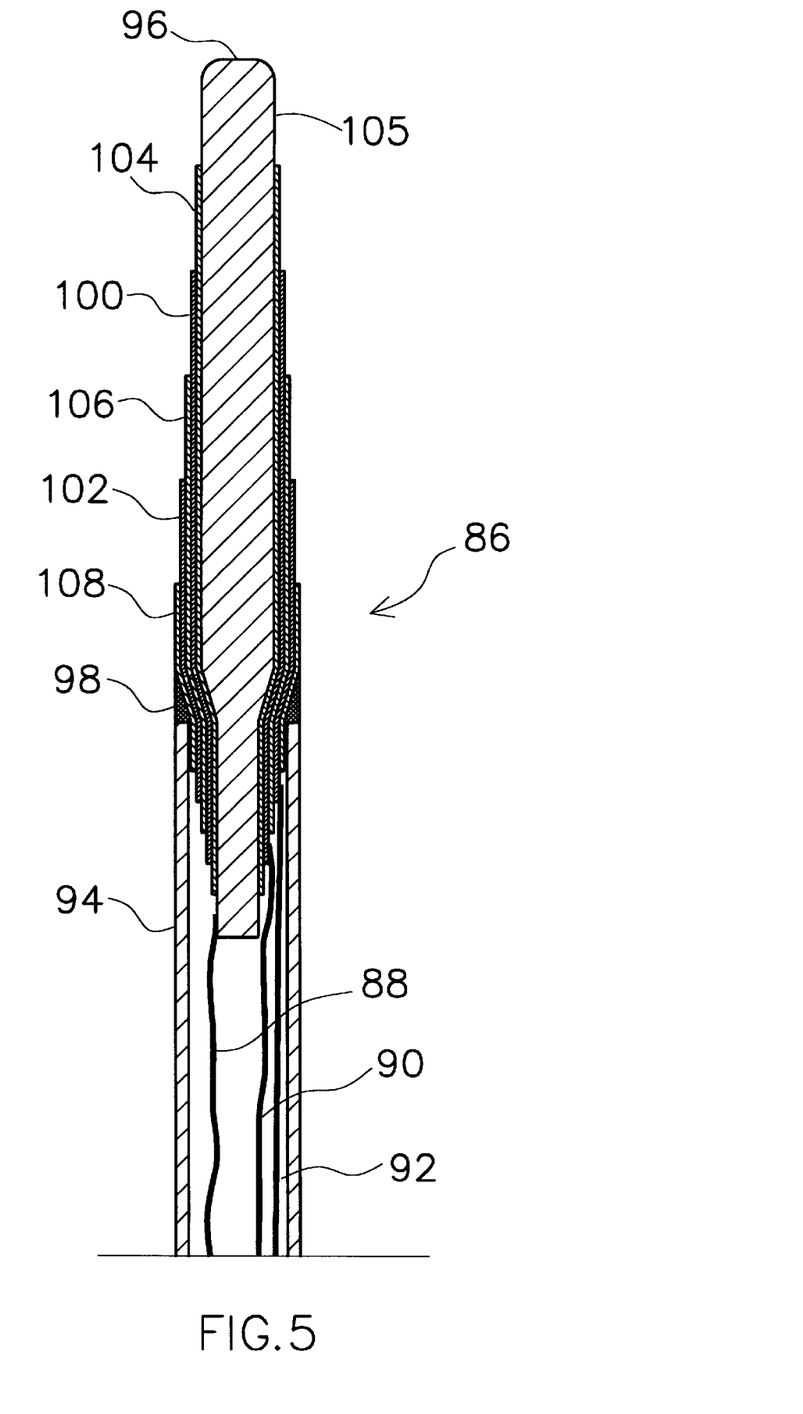
FIG. 5 shows a connector element in cross section.

In another embodiment of the invention the guide wire comprises a separately made proximal connector element, shown in FIG. 5, and generally designated with reference numeral 86. The connector element is inserted in a tube 94 that corresponds to the tube 36 in FIG. 4. The connector 86 is secured to the tube e.g. by gluing 98. Electrical leads or wires 88, 90, 92 are provided inside the tube 94 and extend to the distal end where they are attached to a sensor element, in the same way as shown in FIG. 4. The connector itself is made of a core element 96 provided with alternating concentric conductive layers 100, 102 with insulating layers 104, 106 between them, and an outer insulating layer 108.

Figure 8:
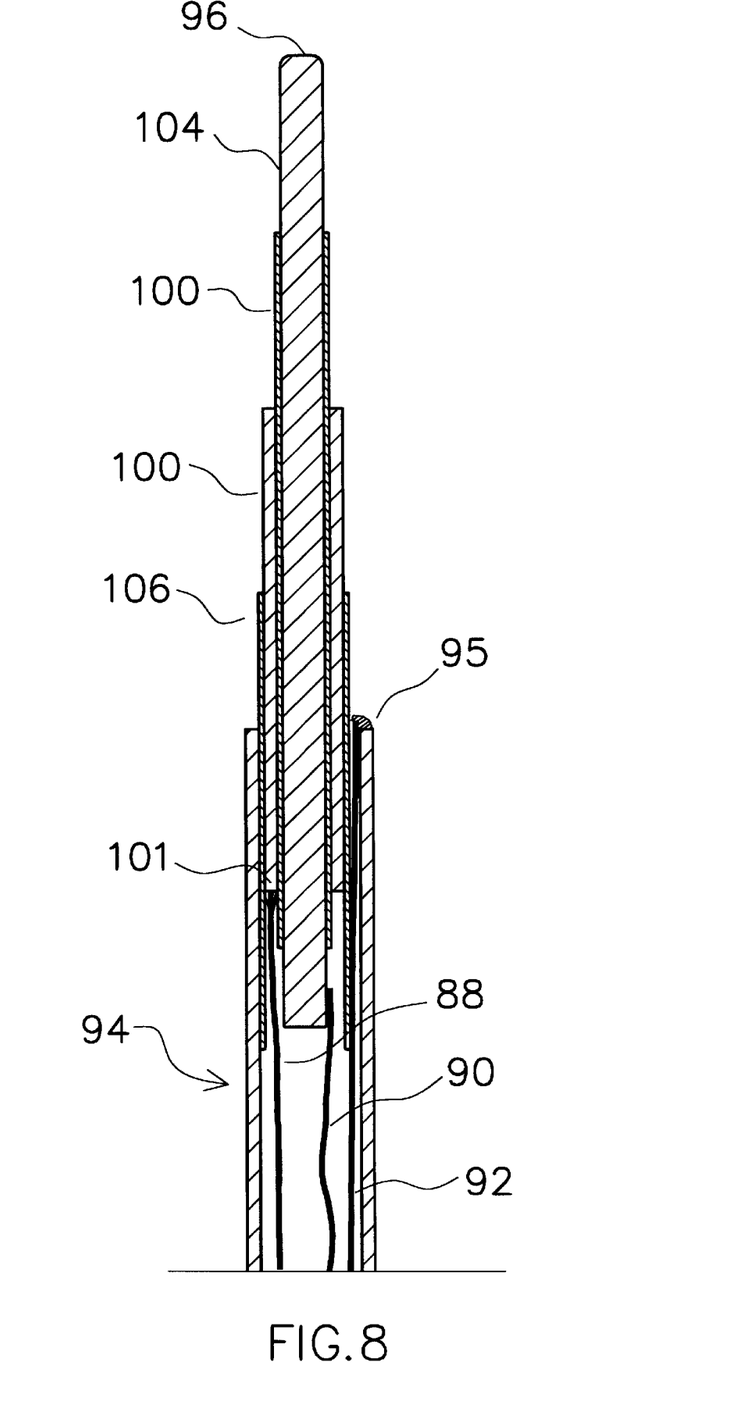
FIG. 8 is a view in cross section of another embodiment of a connector element.

FIG. 8 illustrates an alternative embodiment of the proximal connector member. Here, a core member 96 is provided with an insulating layer 104, as previously described, and a conductive layer 100 has been deposited thereon, and finally an insulating layer 106 has been provided thereon. Electrical leads 88, 90 are connected e.g. by soldering to respective conductive members 100 and 102 respectively. However, lead 92 is connected, e.g. by soldering to the tube 94 at its outer edge 95.

As can be seen in the figure, the last insulating layer 106 extends beyond the edge 101 of the conductive layer 100. This may be achieved by utilizing a shrink tube for insulation instead of deposition of insulating material. The reason for wanting this configuration is that the external tube 94 is used as one of the conductor elements, for engaging with a female connector. If the insulation were not provided in this fashion, there might be a risk for short-circuiting between the two inner solders and the tube 94, although it is not absolutely necessary to provide such insulation.

Figure 9:
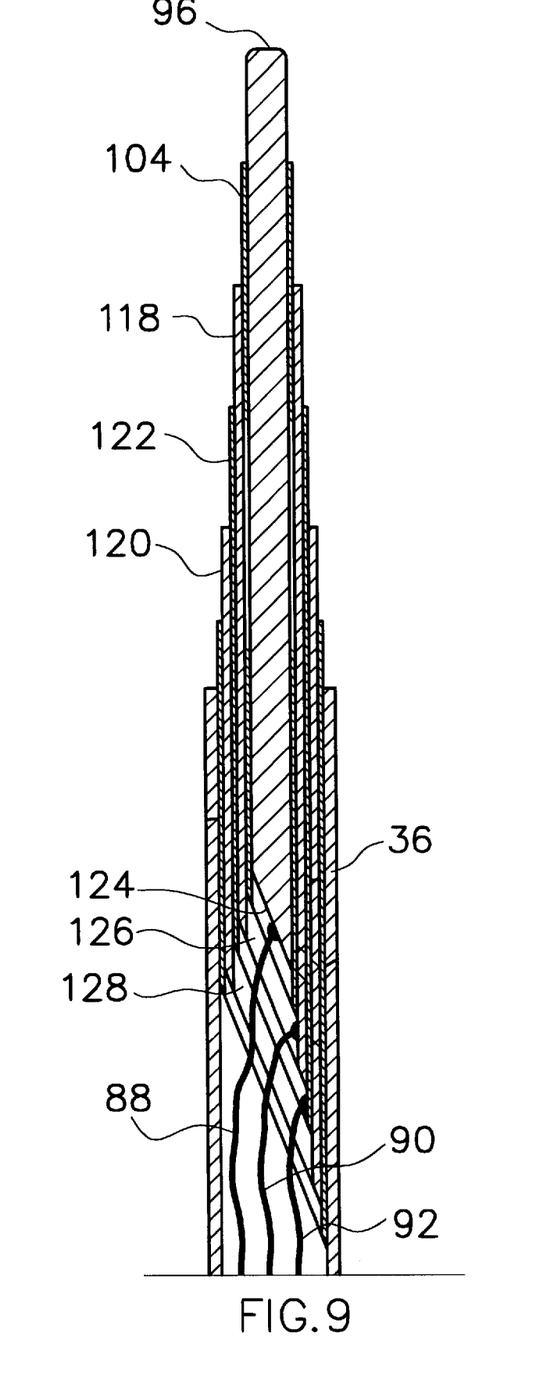
FIG. 9 is a view in cross section of still another embodiment of a connector.

In FIG. 9 there is shown still another alternative embodiment of the proximal connector member. In this embodiment the concentric conductive layers are provided by arranging tube segments 118, 120, preferably metal tubing, of increasingly larger diameter in a concentric fashion on a core element 96.

The core element 96 is first provided with a layer of insulating material 104 either by any of the techniques described below in connection with the method of manufacturing, or by placing a shrink tube on it. Then a metal tube 118, optionally already provided with an insulating layer 122, is provided and the core element 96 is inserted into the tube segment 118. An insulating layer may be provided if not already in place, and the aggregate comprising the core element 96, insulating layer 104 thereon and the first metal tube 118 is inserted in a further metal tube 120. The process is repeated until the desired number of concentric conductive layers have been obtained, in the shown embodiment two tube segments 118, 120 have been mounted on a core member 96.

Electrical leads provided 88, 90, 92 in the guide wire and attached to a sensor at the distal end, are connected to the connector as shown in FIG. 9. Namely, as in the shown embodiment the core element 96 at its distal end may have a beveled surface 124 for facilitating soldering. Furthermore, the tube segments overlap in an inverted fashion compared to the configuration at the proximal end of the connector. Also, the segments have been cut at an angle in order to provide beveled openings 126, 128 for easier access to the inner surfaces of each tube segment for connection of the electrical leads, e.g., by soldering. The entire aggregate of core member 96 and tube segments 118, 120 is inserted in a guide wire tube 36.

The tube segments are preferably glued together, and optionally the glue itself may provide the necessary insulation between the conductive tube segments.

Thus, in this embodiment the inventive concept of concentric conductive layers has been embodied by providing concentric tube segments of conductive material.

Figure 6:
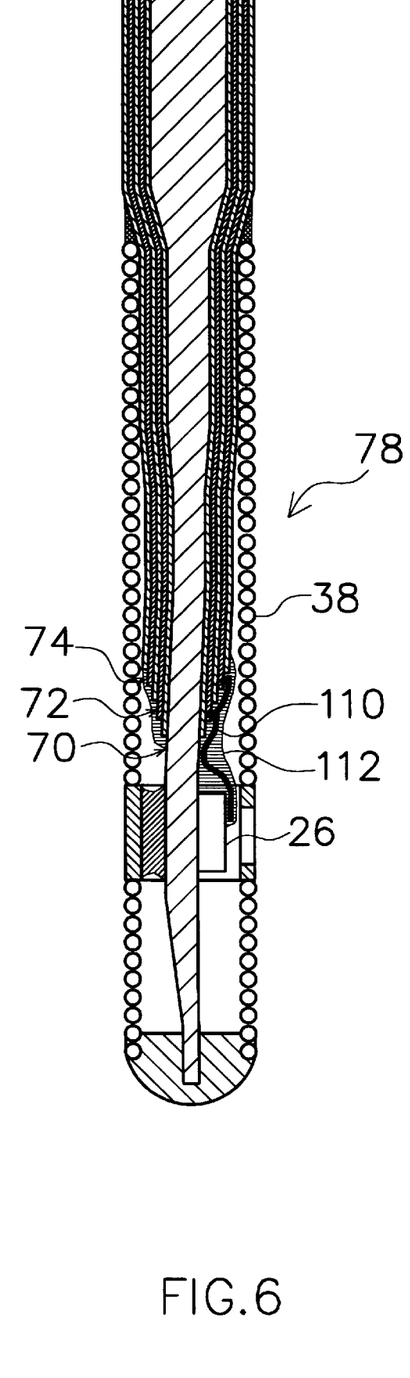
FIG. 6 is a view in cross section of the distal end of a guide wire of the invention showing an improved mounting of a sensor element.

An alternative embodiment for connecting the sensor to the conductors is illustrated in FIG. 6.

Here the connection between sensor chip and contact elements is achieved by using a small flexible circuit board 110, having a pattern of conductors provided on its surface. The circuit board is bonded onto the conductor pattern on the chip 26 and onto said contact members 70, 72 and 74 respectively. The circuit board is securely fixed by providing glue 112 or other suitable insulating material, covering the exposed conductive portions, thereby sealing off to avoid short-circuiting.

Figure 7:
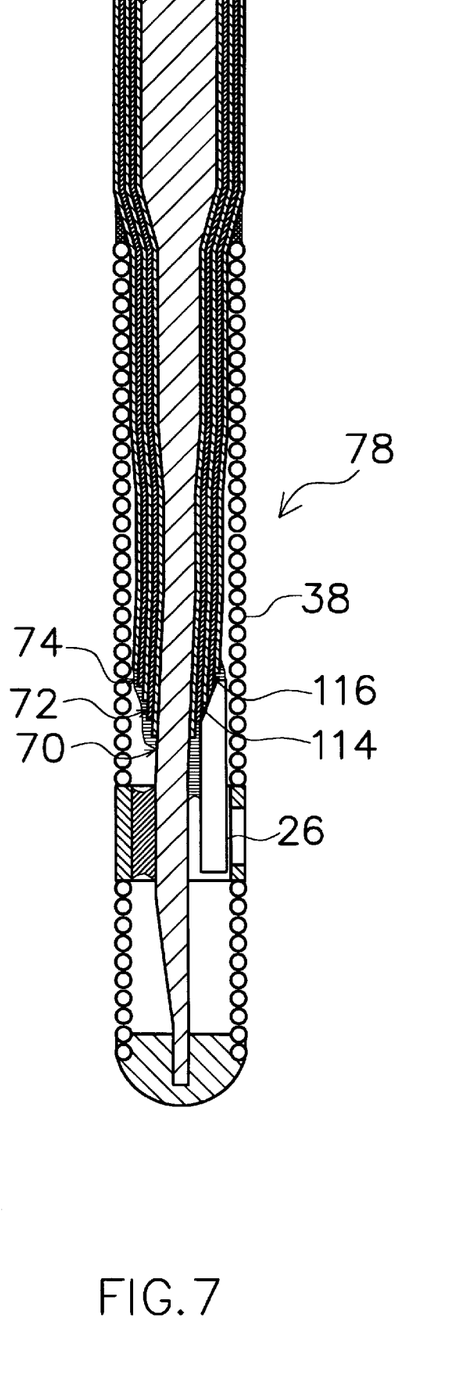
FIG. 7 is a view in cross section of the distal end of a guide wire of the invention showing an alternative of improved mounting of a sensor element.

Still another way of mounting the sensor 26 is shown in FIG. 7. In this embodiment the chip is slightly modified, in that it may be made somewhat longer. Furthermore, it is turned upside down compared to the conventional way of mounting. Thus, the pattern of conductive strips provided on the chip (see International Patent Application WO 97/27802, expressly incorporated herein in its entirety, wherein the design of a miniature pressure sensor is disclosed) is bonded directly onto the contact members 72, 74 at 114 and 116, respectively. It is also possible to make contacts through the sensor chip.

Thus, it is conceivable to design the sensor chip 26 such that it is provided with contact pads located on the bottom surface of the chip body in such a spatial relationship as to fit onto the exposed contact members 70, 72, 74. Said pads are connected to the sensor element on the chip by suitable electrically conductive patterns. The contact may be made by soldering or by bonding or the like. The chip itself may be readily secured onto the guide wire by gluing or the like.

The preferred method of manufacturing a guide wire according to the invention will now be described with reference to the embodiment in FIG. 3.

As mentioned above a core wire made of stainless steel is preferably provided if a conductive core is required. Of course other materials are conceivable provided they exhibit the required compromise between flexibility-stiffness, and the necessary conductivity. In principle any metal or metal alloy meeting the requirements of mechanical properties and electrical conductivity will be adequate. Another suitable candidate may be e.g. carbon fiber, suitably doped.

In the case of a conductive core, to be used as one of the conductors, a first layer of insulating material is deposited circumferentially and along the entire length of the wire 54. The insulating material may be any polymer or other non-conductive material that will adhere sufficiently well to the surface of the core wire.

Thus, a first insulating layer 56 is provided on the core wire 54. This layer is made of a suitable insulating polymer, an example of which is Parylene®, which is a poly-para-xylylene (Parylene N) or poly-monochloro-para-xylylene (Parylene C) obtainable from Paratech Coating Inc., USA. Such a layer is applied by an evaporation process, whereby the polymer is provided as a dimer placed in a vacuum system and converted to a reactive vapor of the monomer. The vapor is passed at room temperature over the objects to be coated, and will rapidly coat them with a polymer.

Examples of other usable methods of application of a polymer layer are spraying or dipping. For example, polyurethane is dissolved in a suitable solvent, such as acetone, and after dipping the solvent is evaporated leaving a thin coating of polymer.

A second layer 62 of a conductive material, e.g., Ni, is then applied by e.g. electroless (chemical) plating or CVD. In the shown embodiment there are two such conductive layers 62, 64 with an insulating layer 58 interposed between them. The inner layer 56 of polymer forms an insulation between core wire 54 and conductive layer 62.

The at present preferred material for the conductive layer is Ni, but other conductive materials are of course conceivable, such as Au, Pt, Cu, doped semiconductors, etc.

Al is also a possible metal. If Al is used it is possible to oxidize the Al to form an insulating layer. A second Al-layer is then deposited on the oxide, the new layer oxidized and so on, until the desired number of layers have been obtained.

Silicon could also be used in the same way as outlined above for Al.

The respective layers preferably have the following thicknesses:

Intermediate polymer layers 6 and 8 1–50 µm
Conductive layers 12 and 14 1–50 µm
Outer insulating layer 10 (or shrink-tube) 10–50 µm The core wire preferably has a diameter of about 0.20 mm at the proximal end, and down to 0.08 mm at the distal end.

There are various possible methods of applying the conductive layer, but at present Chemical Vapor Deposition (CVD) is preferred. Sputtering, electroless plating or evaporation techniques may however be used.

A batch of polymer coated core wires is placed in a CVD reactor and Ni is applied in a circumferentially covering layer. The CVD process itself is well known technology, and it is within the ability of the skilled man to find appropriate working parameters for obtaining the desired properties of the layers, such as thickness, porosity, density stress, the presence of pinholes etc.

When a conductive layer 62 has been applied, the wires are again subjected to an evaporation process for applying a second insulating layer 58. If this layer is to be the outer layer the thickness may have to be made thicker than the first intermediate insulating layer.

On the other hand, if additional conductive layers 64 are required, the CVD process for Ni coating and the evaporation process for polymer coating are repeated the desired number of times, and a final outer insulating layer 60 is provided as the last step.

As indicated above, the outer insulating layer 60 may have to be made somewhat thicker than the intermediate layers of insulating material, primarily in order to serve as a protective layer on the finished guide wire.

As an alternative embodiment, the core wire may be non-conductive. In this case the wire can be made of polymer or glass fiber, provided the material meets the same material property requirements as indicated above. Carbon fiber is also conceivable in this case provided its conductivity is low enough. Combination materials such as braided polymers (polymer material reinforced with metal threads or fibers) could also be used.

The manufacturing process described above can be carried out on a large number of wires in a batch mode, which of course significantly lowers production costs compared to the currently used production methods which are mainly manual and thus extremely labor intensive. Also, and not less important, the rejection rate of produced items may be significantly reduced.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

In particular, the concentric layers of electrically conductive material may be provided as concentric tube segments of conductive material arranged around a core element, and having insulating material interposed between the tubes. Thus, a "concentric tube segment" shall be considered as equal to a "concentric layer" for the purposes of the present invention, as described and defined herein.

What is claimed is:

1. A guide wire for intravascular investigations comprising:

an elongated element;

at least one electrical conductor extending along a length of said guide wire;

wherein at least a portion of one of said at least one electrical conductor is provided as a layer of electrically conductive material, extending concentrically over the circumference of, and along said elongated element forming a part of said guide wire and wherein said layer of conductive material is provided on a proximal end of said elongated element, and wherein each layer of conductive material is connected to a respective electrical lead extending along said elongated element to a distal end thereof.

2. The guide wire as claimed in claim 1, wherein the at least one conductor includes electrical leads extending over the portion of the length of said guide wire not provided with said layer of conductive material.

3. The guide wire as claimed in claim 1, further comprising a core wire, wherein said layer of conductive material is provided as a concentric layer on said core wire.

4. The guide wire as claimed in claim 1, further comprising an insulating layer on said layer of conductive material.

5. The guide wire as claimed in claim 3, wherein the distal portion of the core wire has a smaller diameter than the proximal portion of said core wire.

6. The guide wire as claimed in claim 3, wherein the core wire is conductive.

7. The guide wire as claimed in claim 3, wherein the core wire is non-conductive.

8. The guide wire as claimed in claim 1, further comprising an electric sensor connected at the distal end.

9. The guide wire as claimed in claim 8, wherein said sensor is a pressure sensor.

10. The guide wire as claimed in claim 8, wherein the layer of conductive material is exposed at the distal end to form a contact element to which the sensor is electrically connected.

11. The guide wire as claimed in claim 10, wherein the layer of conductive material is connected to the sensor by bonding or soldering electrical leads to said contact elements.

12. The guide wire as claimed in claim 10, wherein the layer of conductive material is connected to the sensor by providing a flexible circuit board provided as a bridge between the sensor and the contact members on the exposed layer portions.

13. The guide wire as claimed in claim 10, wherein the layer of conductive material is connected to the sensor by bonding the sensor directly onto said contact elements.

14. The guide wire as claimed in claim 3, wherein each layer of conductive material is exposed in a consecutive manner at the proximal end of the guide wire, and present a contact surface extending circumferentially around the core wire to form a contact element adapted to be engaged by a female connector.

15. A guide wire for intravascular investigations comprising:

a core wire;

a plurality of electrical conductors extending along the length of said core wire;

an electrical sensor provided at the distal portion of said guide wire and connected to said conductors; and     a male connector means provided at the proximal end of said guide wire;

wherein said electrical conductors are provided as concentric layers around said core wire substantially along the length of said core wire, and with insulating layers interposed between said conductive layers; and     wherein said male connector means is provided as ring shaped exposed portions of said conductive layers, with segments of insulating material separating said ring shaped portions in the longitudinal direction.

* * * * *